US008501000B2

(12) United States Patent
Hein et al.

(10) Patent No.: US 8,501,000 B2

(45) Date of Patent: Aug. 6, 2013

(54) METHODS AND DEVICE EMPLOYING CENTRIFUGAL FORCE

(71) Applicant: Roche Molecular Systems, Inc., Pleasanton, CA (US)

(72) Inventors: Heinz-Michael Hein, Huenenberg See (CH); Emad Sarofim, Hagendorn (CH); Lotar Schenk, Knonau (CH); Hans-Peter Wahl, Huenenberg (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/648,865

(22) Filed: Oct. 10, 2012

(65) Prior Publication Data

US 2013/0037471 A1 Feb. 14, 2013

Related U.S. Application Data

(62) Division of application No. 12/617,530, filed on Nov. 12, 2009, now Pat. No. 8,313,652.

(30) Foreign Application Priority Data

Nov. 12, 2008 (EP) .................................... 08105782

(51) Int. Cl.
*B01D 21/26* (2006.01)
*B01D 35/06* (2006.01)
*G01N 33/543* (2006.01)

(52) U.S. Cl.
USPC ............. 210/223; 210/222; 210/695; 422/72; 422/533; 422/548; 422/544; 436/45; 436/526

(58) Field of Classification Search
USPC .................... 210/222, 223, 695; 422/72, 533, 422/548, 554; 436/45, 526
See application file for complete search history.

(56) References Cited

U.S. PATENT DOCUMENTS 5,224,604 A 7/1993 Duczmal et al.
5,866,000 A 2/1999 Yeh
6,150,182 A 11/2000 Cassaday

FOREIGN PATENT DOCUMENTS

EP 837871 B1 5/2003
EP 2186570 A1 5/2010
WO 2005079995 A1 9/2005

*Primary Examiner* — David A Reifsnyder
(74) *Attorney, Agent, or Firm* — M. Reza Savari

(57) ABSTRACT

The present invention includes a container and a method of separating one or more components of interest bound to magnetic particles using centrifugal forces.

8 Claims, 7 Drawing Sheets

METHODS AND DEVICE EMPLOYING CENTRIFUGAL FORCE

RELATED APPLICATIONS

This application is a divisional of application Ser. No. 12/617,530, filed on Nov. 12, 2009, now U.S. Pat. No. 8,313,652, which claims the benefit of European Patent Application 08105782.0, filed on Nov. 12, 2008, the disclosures of which are incorporated by reference in their entirety for all purposes.

BACKGROUND OF THE INVENTION

The object of the invention is a method for separating a component of interest bound to magnetic particles from a liquid sample by applying magnetic and centrifugal forces, wherein the centrifugal force is diametrically effective to the direction of the force which is effective to the magnetic particles by the magnetic field, and the magnetic force is higher than the centrifugal force effective to the magnetic particles, and thereby separating the magnetic particles from the liquid. The separated liquid is detained by a trap, the trapped liquid is preferably in addition bound to an adsorptive material. A further object of the invention is a device for carrying out the method.

Methods for isolating biological materials, especially nucleic acids from their natural environment with the help of magnetic particles are known since years (e.g., EP 0 837 871). According to the known methods, the sample mixture comprising the component of interest to be separated is brought into contact with the magnetic particles, mixed and incubated, under conditions where the compound of interest binds to the particle, for a period of time sufficient for the binding to occur. After incubation, the biological material bound to the magnetic particles is usually separated from the fluid by using a magnetic field. For instance, the magnetic particles can be pulled to the wall of the vessel or a pipette in which incubation was performed. The fluid containing the sample contents not bound to the magnetic particles are subsequently eliminated, e.g., via a pipette by aspiration.

These procedures have, however, a disadvantage in that a particular amount of the magnetic particles are sticking to the reaction vessel and/or the pipette tip.

Another disadvantage of removing the sample fluids by pipetting or aspiration is that either extensive assemblies, e.g., robotic machines, are required or the deficiency of manual handling has to be accepted. Moreover, extended time is required to draw magnetic particles out of the liquid or suspension by applying magnetic forces and to have those subsequently sufficiently washed (usually 3 to 4 times). Another disadvantage is that the magnetic particles collected mass or clumps tend to retain excessive fluid, the clumped mass is difficult to resuspend into solution.

U.S. Pat. No. 5,098,845 (Babson) describes a circular vessel containing a rather large sphere (solid support) to which specific analytes, e.g., antibodies, are attached. Washing separation is effected by rotating the cup about its longitudinal axis where centrifugal force serves to remove the liquid contents while the solid material remains in the vessel. The method has, however, the disadvantage similar to coated containers in that the surface area available for binding is limited to the dimension of the sphere. Yet another disadvantage is that the coated vessel cannot be used for micro spheres and especially not for magnetic micro spheres.

U.S. Pat. No. 6,150,182 (Cassaday) describes a method for combining magnetic and centrifugal extraction techniques in a manner that improves wash efficiency and reduces disadvantages of stand alone magnetic or centrifugal systems. A disadvantage of the method is, however, that it is difficult, if at all possible, to automate the procedure. Moreover, the method described by Cassaday does not overcome the disadvantages which are associated with the method of removing the sample fluids by pipetting or aspiration.

The devices and methods known have the disadvantage that they do not allow the separation of a component of interest bound to magnetic particles from a solution in an easy, sufficient manner without the need of any robotic means or without the risk involved with manual handling of samples.

SUMMARY OF THE INVENTION

The invention is directed to a method for separating a component of interest, e.g., derived from a biological sample like plasma, blood or urine, bound to magnetic particles from a solution which combines applying magnetic and centrifugal forces, whereby the latter are diametrically directed to each other.

In a first embodiment the invention is directed to a method for separating a component of interest bound to magnetic particles from a solution in particular comprises the following steps:

(a) providing a container device having (I) one or more flat chamber(s) each comprising an interior volume, an angular bottom ascending (8) to the outer part of the compartment and means for trapping fluids (10), said angular bottom having preferably an angle between 1° and 85°, said means is positioned at the inner side of the outer part of the compartment of the container and (II) a magnet positioned at the outer side of the inner part of the compartment of the container for capturing the magnetic particles and the component of interest bound to said magnetic particles, (b) disposing at least a portion of said solution including the component of interest, and if necessary possible additional reagents, in the interior volume of said chamber(s), before said container is rotating around an axis located outside the inner part of said container and adjacent to the magnet, (c) adding to the solution comprising the component of interest a multiplicity of magnetic particles before said container is rotating around an axis located outside the inner part of said container, said magnetic particles being coated with a reaction component that binds said component of interest, (d) mixing said solution with said multiplicity of coated magnetic particles to thereby producing a mixture comprising magnetic particles and a supernatant liquid, and, thereafter (e) separating the magnetic particles and the liquid by:
    spinning the mixture of magnetic particles and the liquid within said container by rotating said container such that at least one portion of said liquid is expelled to the outer part of said container, wherein part or all of the liquid is trapped by means integrated in the interior volume at the outer part of the container only while said liquid is forced by centrifugal forces (13) into the trapping means and a magnet field is applied such that magnetic particles bind to the inner side of the inner part of said interior volume.

In another embodiment the invention is directed to a container device for separating a component of interest bound to magnetic particles from a solution, said container device is consisting of:

(1) a container having one or more chamber(s) each with an interior volume, an angular bottom ascending to the outer part of the chamber and means for trapping fluids, said means is positioned inside the outer part of the chamber(s) of the container, (2) a magnet positioned at the outer side of the inner wall of the chamber of the container for capturing the magnetic particles and the component of interest bound to said magnetic particles, (3) a rotating axis located at the centre of said container adjacent to the magnet, and (4) means for applying a magnetic field, e.g., a magnetic force (14) on the magnetic particles (21), and an engine for rotating said container.

DETAILED DESCRIPTION OF THE INVENTION

Figure 1:
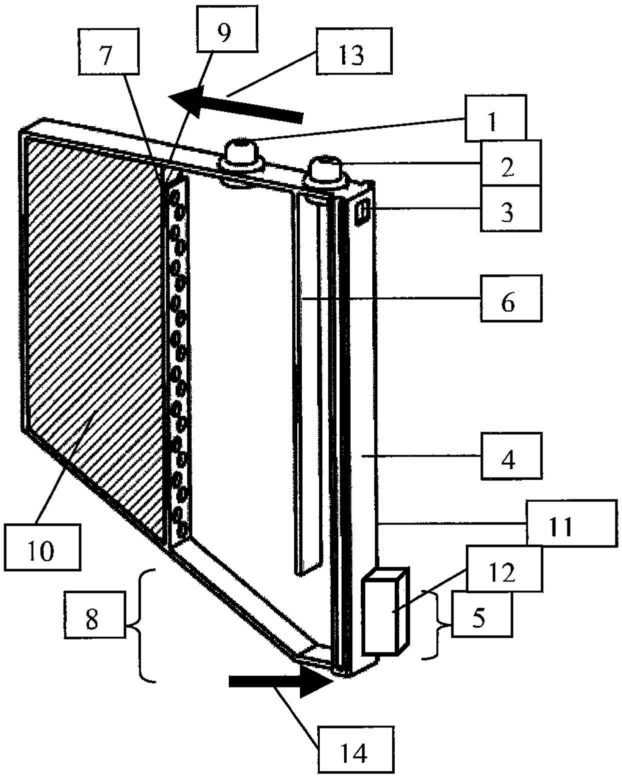
FIG. 1 shows a single chamber (cartridge) and the position of the magnet according to the invention.
Figure 2:
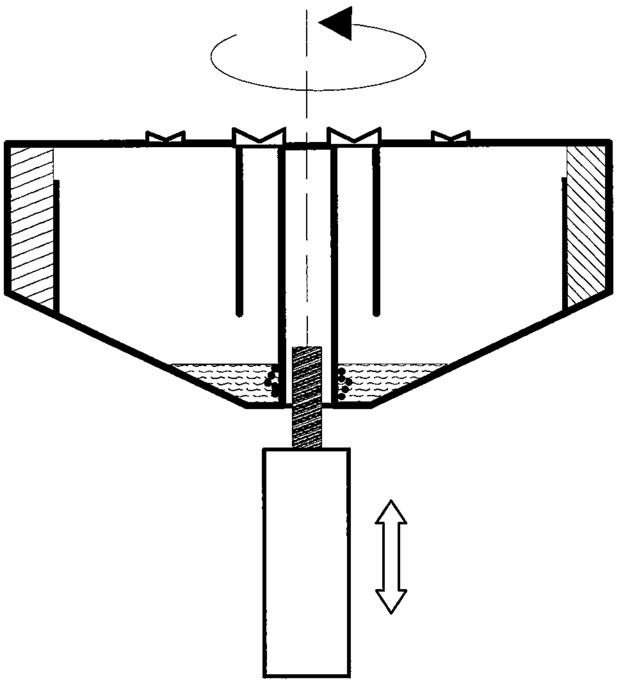
FIG. 2 shows a cross section of cartridges arranged in ring-form with a removable magnet in the centre according to the invention.
Figure 3:
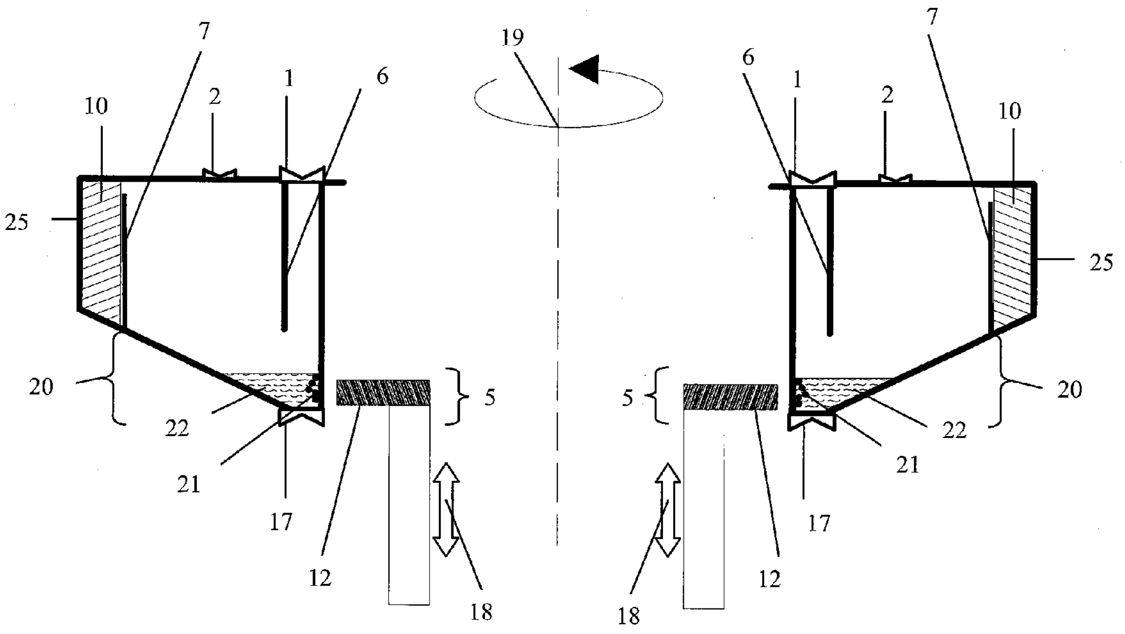
FIG. 3 shows a cross section of two cartridges in more details, including the rotation axis and the removable magnet.

The container device suitable for the method for separating a component of interest comprises one or more compartments being flat chambers each comprising an interior volume, an angular bottom, an ascending part of the lower part of the chamber (8), ascending to the outer part of the compartment and means for trapping fluids (10). Each of the flat chambers comprises a cover (23) with a first pipetting opening (1), located adjacent to the inner barrier (6), and a second inner pipetting opening (2), both optionally covered with a flexible sheet of film material or a material made of a thermoplastic elastomer. In some of the devices according to the invention there is in addition a pipetting outlet (17) at the lowest part of the ascending bottom of each chamber.

The interior volume suitable to be used as a reaction chamber is positioned adjacent to the inner part or wall (4) of the compartment, whereas the means for trapping fluids (10) are positioned inside the outer wall (25) of the compartment of the chamber. Depending from the size of samples or the particular application, the dimension of the chambers and the lower part of the chamber (5) can be modified accordingly. A typical chamber contained in the device suitable for the inventive method comprises an inner wall (4) with a height of 3 to 13 cm, and a thickness between 5 and 25 mm, an outer wall (25) oppositely and in parallel located to the inner wall (4) having a height of 2 to 12 mm and a thickness between 5 and 80 mm. Next to the inner wall (4) of the chamber a inner barrier (6) is affixed to separate the pipetting openings (1) and (2). The inner and the outer walls (4), (25) are connected by appropriately formed parallel side walls resulting in a surface distance from the inner wall to the outer wall of 2 to 12 cm.

Means for trapping fluids (10) of liquids or fluids moved by centrifugal force to the outer part of the compartment according to the present invention is a physical wall with a gap (9) in the upper part of the cut off trench (7), preferably not reaching the top of the chamber in the interior volume of said chamber. The material of said means for trapping fluids (10) is preferably based on a chemical adsorbent material or a hyper adsorbent material suitable to irreversible bound sample fluids, including substances which were not bound to the magnetic particles, the latter are forced to the inner part of the compartment next to the magnet (12). After centrifugation the sample liquid, including all other liquids and non-magnetic ingredients, is enclosed in the adsorbent material and the material of interest is bound to the magnetic particles. The component of interest bound to the magnetic particles can subsequently be washed and further processed.

The magnet (12) positioned at the outer side of the inner wall (4) of the compartment of the container during the separation process can be switched off, e.g., by removing the magnet downwards. Consequently, any magnetic particles (21) concentrated and captured in the lower part of the chamber (5) at the inner side of the inner wall (4) of the compartment before removing the magnet will be released into the fluid of the interior volume in the lower part of the chamber (5). The fact that the magnetic field applied can be easily switched on and switched off, e.g., by moving the magnet up and down, is in particular important for washing or mixing the magnetic particles with the component of interest bound to the magnetic particles.

When at least one portion of a solution including the component of interest is disposed in the interior volume of one or more chamber(s), the magnet (12) positioned at the outer side of the inner wall of the compartment of the container is switched on, while the container device is rotating around an axis (19) located outside the inner part of said container. Preferably, the magnet is rotating around the same axis at the same time when the container device is rotated such that at least one portion of the sample liquid is expelled to the outer wall of the container, which results in a homogenous magnetic field in each of the chambers.

The spinning movement applied to the mixture comprising the magnetic particles (21) as well as the sample liquid or reaction solution (22) is preferably such that the resulting centrifugal forces are identical or lower than the magnetic force being effective on the magnetic particles inside said mixture and sufficient to transport the non-magnetic liquid part of said mixture to said trapping means (10). The centrifugal forces are usually modified by varying the speed of the rotation movement. Preferably, centrifugal forces between 1 g and 100 g, more preferably between 6 g and 80 g, are applied.

A multiplicity of magnetic particles (21) being coated with a reaction component that binds the said component of interest is added to the solution comprising said component of interest. During the addition of the magnetic particles the magnet is preferably switched off and the rotating movement of the device is neutral.

The component of interest can be any analyte worth to be determined, e.g., a nucleic acid, an oligo- or polynucleotide, a protein, an antibody, an antigen or hapten or any other component capable of being bound, directly or indirectly, to magnetic particles.

For certain applications the flat chamber is equipped at the bottom of the chamber with an additional tube (15) for performing a subsequent reaction, e.g., a PCR reaction. The bottom of the lower part of the chamber (4) has an opening (16) where the reaction mixture can be easily transferred into the reaction tube (15). The component of interest bound to the magnetic particles is usually transferred to said additional tube through the outlet at the lowest part of the ascending bottom of the chamber.

A further object of the invention is a circular container device for separating a component of interest bound to magnetic particles from a solution, said container device is consisting of:

(1) a container having one or more chamber(s) each with an interior volume, an angular bottom ascending to the outer part of the compartment and means for trapping fluids (10), said means is positioned inside the outer wall (25) of the compartment(s) of the container, (2) a magnet (12) positioned at the outer side of the inner wall (4) of the compartment of the container for capturing the magnetic particles (21) and the component of interest bound to said magnetic particles, (3) a rotating axis (19) located at the centre of said circular container adjacent to the magnet (12), and (4) means for applying a magnetic field, e.g., a magnetic force to the magnetic particles, and an engine for rotating said container.

The container device according to the present invention comprises one or more chamber(s) each having a volume in the range of 1 ml and 50 ml, more preferably in the range of 5 and 25 ml.

Preferably, the container device comprises multiple chambers combined in one or more single cassettes or cartridges, each cassette or cartridge is connected or connectable to one or two others of such cassettes. The cassettes are preferably consisting of two or more up to 100 chambers. Preferably, said cassettes are comprising 8, 12, 24, 48, 72 or 96 chambers and can be arranged in a linear or ring-formed array.

A particular preferred embodiment according to the invention is that the multiple chambers containing connectable single cassettes form a ring of 4, 8, 12, 16, 32, 64 or up to 96 single inter connectable containers. Those cassettes or cartridges are preferably flexibly linked to the respective adjacent cartridge(s), and are either structured in parallel, or preferably are located on a ring around the rotating axis (19), each cassette being individualized. The connection between the single containers is preferably achieved by assembling the channel (27) on one side of the container with the nose strip (26) of another container forming a hinge (28).

The chamber(s) used for the inventive device are usually flat and comprises an angular bottom ascending to the outer part of the compartment. The angle between the angular bottom and the inner wall (4) of the chamber is preferably between 1° and 85°, more preferred between 1° and 60°. A typical chamber contained in the inventive device comprises an inner wall (4) with a height of 3 to 13 cm, and a thickness between 5 and 25 mm, an outer wall (25) oppositely and in parallel located to the inner wall (4) having a height of 2 to 12 cm and a thickness between 5 and 25 mm. The inner and the outer walls (4), (25) are connected by appropriately formed parallel side walls resulting in a surface distance from the inner wall to the outer wall of approximately 2 to 12 cm.

In another preferred embodiment one or more of the chamber(s) comprise at least one inlet and one outlet or inlet port (1, 2, 17), one or more of the ports might be covered with a flexible sheet or film material.

The container device may be further equipped with a vent opening (3) for ventilation which is especially helpful when the container is filled with a large volume of liquid and when the inlet and outlet ports (1, 2, 17) are closed after use. The latter is especially recommended when virological samples are intended to be separated and filled into the containers. The vent opening (3) is preferably consisting of a porous plastic, fleece, fibers material or a porous metal.

The magnet (12) used to bind the magnetic particles (21) to the inner wall (4) of the lower part of the chamber (5) during centrifugation is positioned at the outer side of the inner wall (4) of the compartment of the container. The magnet (12) is further preferably located between the rotating axis (19) and the inner part of said container device. In another embodiment the rotating axis (19) and the magnet (12) are both located at the centre outside the inner part of said container.

Figure 4:
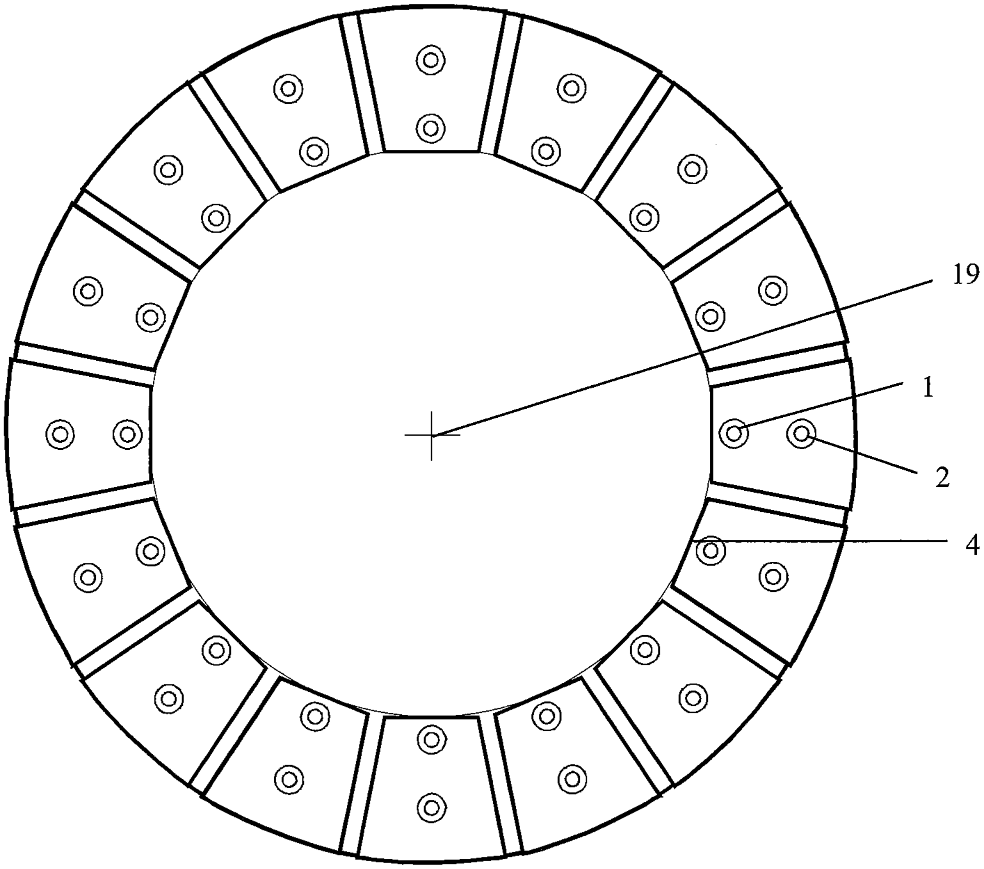
FIG. 4 shows a top view of a ring of cartridges with 16 individual chambers.
Figure 5:
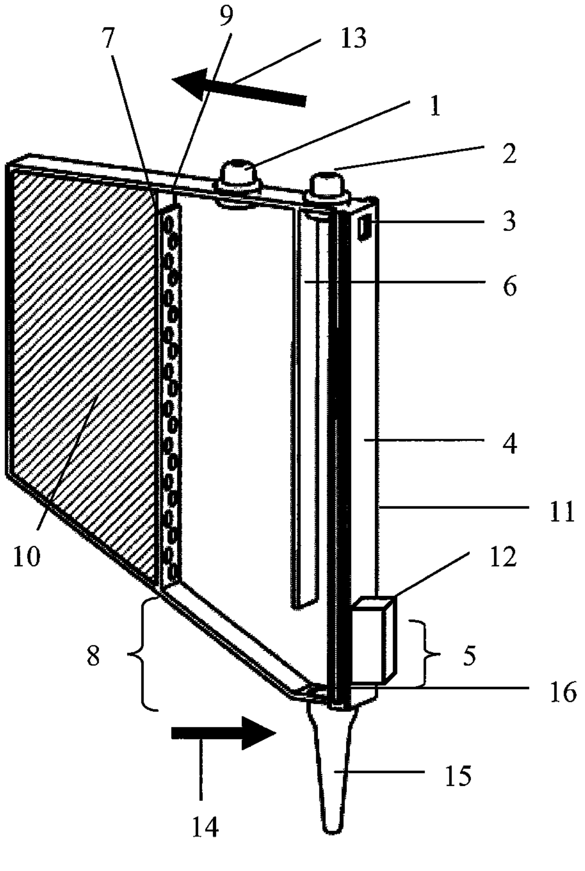
FIG. 5 shows a single chamber (cartridge) and the position of the magnet according to the invention with a reaction tube (15) attached to the lower part (5) of the chamber.
Figure 6:
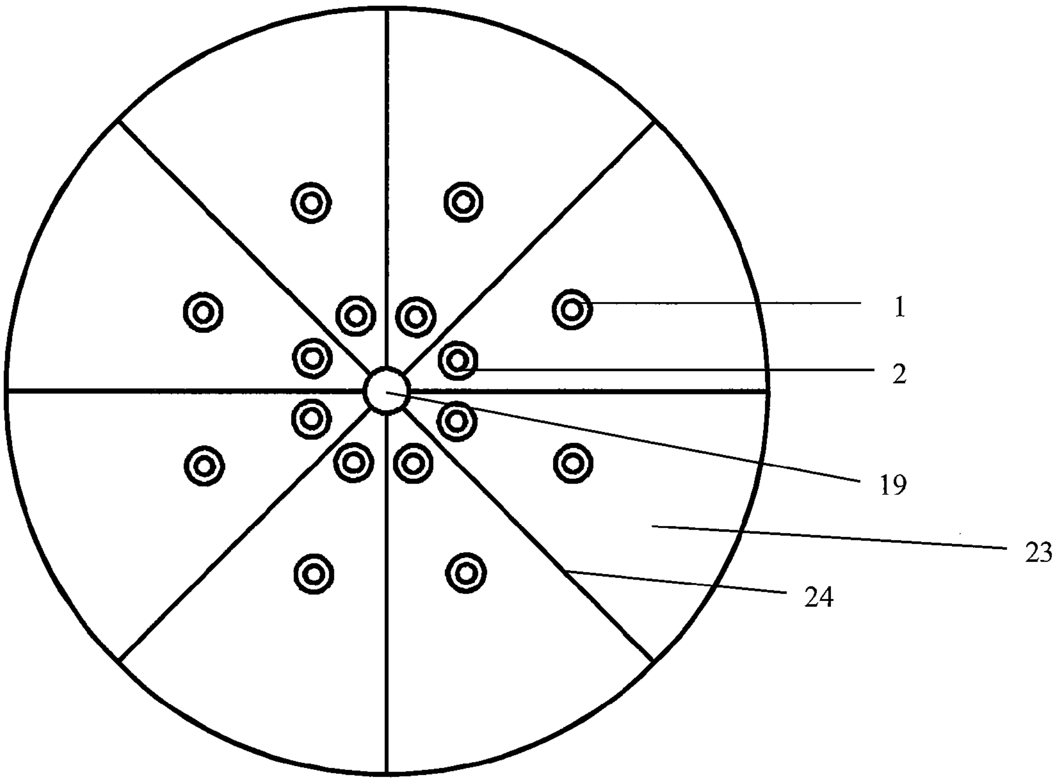
FIG. 6 shows a top view of a compact cartridge with 8 separation chambers.
Figure 9:
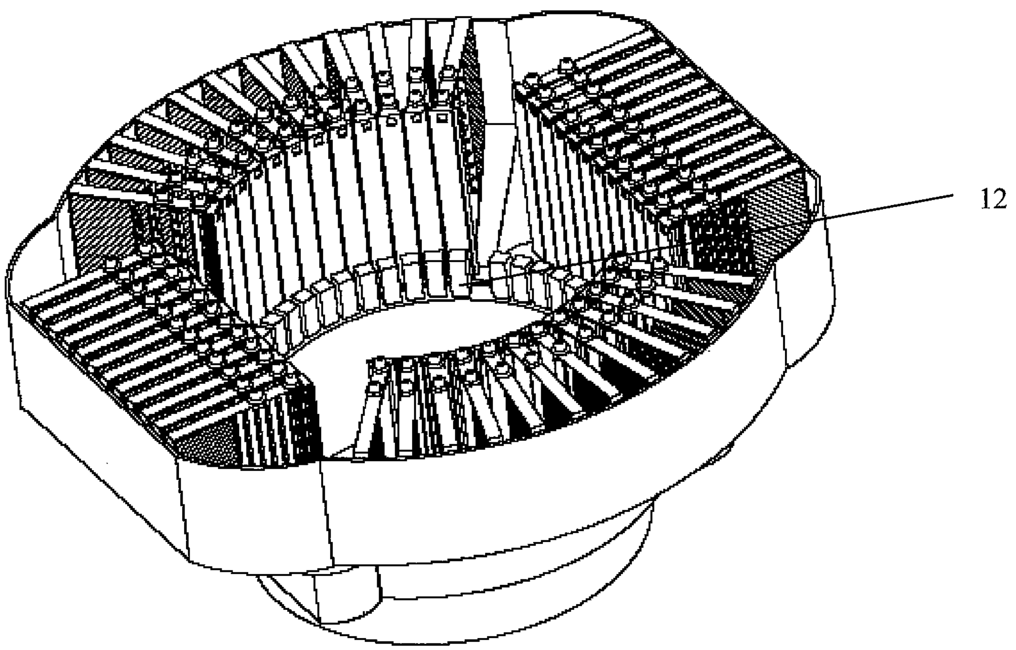
FIG. 9 shows a rotor device according to the invention, wherein the first and third twelve connected chambers are arranged in pipetting position and the second and fourth twelve connected chambers are arranged in spinning position.

In one of the ring-shaped embodiments, the ring of cassettes or cartridges consists of more than two chambers, the device is in particular suitable for the sample preparation of the LightCycler instrument (FIG. 4). In another linear embodiment, where, e.g., 2, 4, 6 or 8 linear array of chambers are spun on a rectangular rotor, the device fits in high throughput instruments, where the samples are subsequently processed by a linear pipetting head with, e.g., 2, 4, 6 or more pipettes on one linear pipetting head and the amplification is subsequently performed on a microtiter plate format thermocycler instrument. In still another embodiment suitable for microtiter plate format devices the linear arrangement, which is also required during the pipetting phase of the process, is bent at the hinge to form a part of a ring so that all cassettes (and chambers incorporated in the cassettes) have the same distance from the rotation axis resulting in a process where all reactions are performed with the same centrifugal force and all compartments are administered to the same magnetic field. Such an embodiment is partially shown in FIG. 9.

Figure 7:
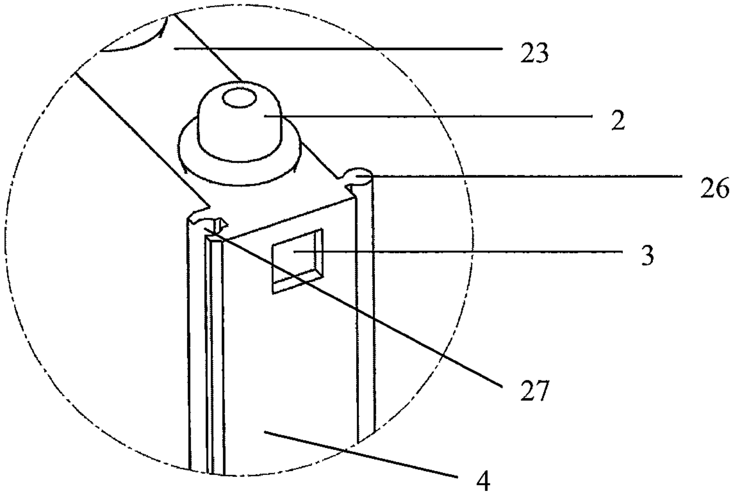
FIG. 7 shows a detail of the upper part of one single inter connectable cartridge.
Figure 8:
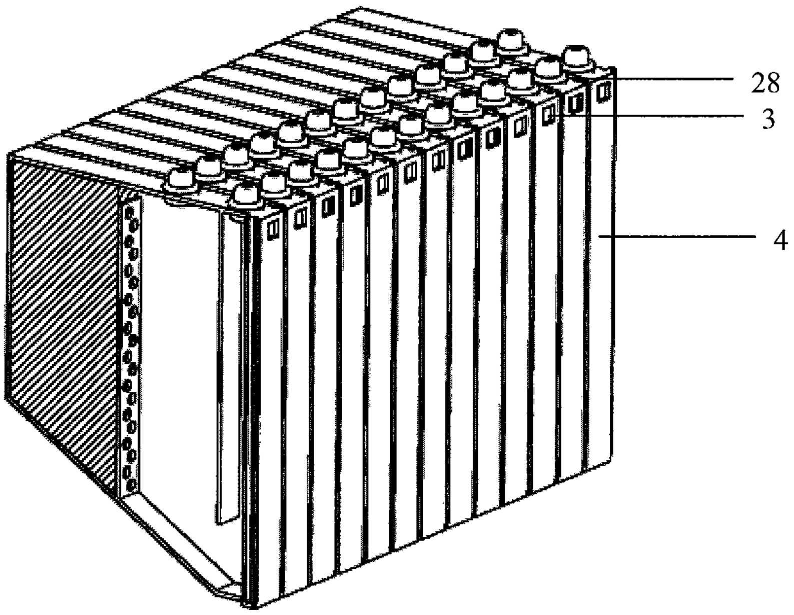
FIG. 8 shows inter connected cassettes in a linear array, prepared for being pipetted by a pipetting device.

A particular embodiment of the present invention is a circular device comprising twelve chambers, a fleece material for the absorption of or trapping the fluid (10) (e.g., a superabsorber material) in each of said chambers and two flexible sheets covering a first and a second inlet and/or outlet ports (1, 2) at the upper cover (23) of said chambers (FIG. 7). Each of the twelve chambers, as shown in FIG. 1 and FIG. 8, of the circular device comprises an angular bottom ascending to the outer part of the compartment and means for trapping fluids (10) positioned at the inner side of the outer wall (25) of the compartment of the container separated from the lower part of the chamber (5) by a cut off trench (7) with a gap (9) in the upper part of the trench (7). At the outer side of the inner part of the container of the device a magnet removable up and down is located. The sample solution comprising the component of interest and the reagents including the magnetic particles (21) is added to the chamber through the first inlet port (1) located closer to the outer part of the chamber. After having combined and mixed the solution comprising the component of interest with the magnetic particles (21) and other reagents required, the device is slightly rotated while the rotating magnet (12) is placed in position. Due to the presence of the magnet (12) in the centre of the device the magnetic particles (21) including the component of interest are bound to the inner side of the inner wall (4) of the compartment. Due to the slight or moderate rotating movement of the device the remaining solution or fluid is transported to the adsorptive material (10) positioned at the inner side of the outer wall (25) of the compartment. This separation process by applying magnetic and centrifugal forces takes only a few seconds, usually between about 3 and 30 seconds. The dried magnetic particles (21) bound to the inner side of the inner wall (4) of the container are preferably suspended with an elution buffer after the magnet (12) has been removed. After an additional mixing and incubation step the eluate can be removed, e.g., with pipetting tips, either together with the magnetic particles (21) in suspension or, if the magnet (12) is put into its place again, without the magnetic particles. The purified eluate is collected through the second port (2) covered by a flexible sheet or film material.

Another embodiment of the present invention is a device comprising multiple chambers arranged on a ring structure. The construction and size of the chambers corresponds to those described above, except that another outlet port (17) covered by a flexible sheet or film material is located at the bottom side of each chamber. Consequently, the purified eluate can be directly transferred into vessels or containers connected with the port at the bottom side of the inventive device, where the component of interest separated can be further processed (e.g., purified nucleic acid could be amplified).

The chamber(s) of the device according to the invention are usually manufactured by injection moulded parts (e.g., as described in "Handbuch Spritzgiessen", Hanser Publ. 2004, page 77 ff; "Werkstoff-Führer Kunststoffe" Hanser Publ. 2001. 8. Ed., pages 83-89) and thus are very cost effectively.

Another object of the invention is an instrument comprising a container device suitable for separating a component of interest bound to magnetic particles from a solution. The instrument for processing a large number of samples with the component(s) of interest is equipped with a pipetting device which has multiple pipetting tips. Those automated pipettes are arranged in a linear way. The turntable to spin the cassettes is equipped with 4 times twelve positions to spin the cassettes. Twelve of the interconnected cassettes are being processed by the pipetting device at the same time. For the pipetting procedure the interconnected cassettes are arranged in a linear way so that the pipetting head with twelve pipetting devices can process twelve cassettes at the same time. After processing all four blocks of twelve cassettes the linear arranged cassettes are bent onto the turntable to allow better processing. The cassettes are located on a segment of the turntable. Now the actual separating process can be performed, the cassettes have all the same distance to the spinning axis, the magnets are put to the outer side of the inner wall of the cassettes. Consequently, 48 cassettes can be processed at the same time, the non desired liquid is transported to the absorbing material at the outer part of the chamber where the liquid is bound to the liquid absorbing material. After the separation the cassettes are bent back to a linear array, in this position further steps like adding the washing buffer and mixing can be performed. The twelve pipetting devices function to add the washing buffer and/or the elution buffer, if requested several portions, to the first twelve cassettes. After the magnetic particles are suspended for all 48 cassettes again the next separation can be performed as described before.

At the end of the process 48 samples (or less, if requested) are performed and all the compounds of interest are separated and purified from the inhibiting material and are being concentrated in the elution solution.

The following example further describes the inventive method and device: Isolation and Purification of viral DNA with COBAS AmpliPrep/COBAS TaqMan Test The reagents were used according to the prescription of the manufacturer Reagents Used:

Lysis buffer: 1.6 ml
Sodium citrate dehydrate pH=4.8
42.5% Guanidine thiocyanate
<14% Polydocanol
0.9% Dithiothreitol
Proteinase solution: 100 ul
Tris buffer pH=5.2
<0.05% EDTA
Calcium chloride
Calcium acetate
7.8% Proteinase
Glycerol
Binding buffer: 820 ul
Sodium citrate dehydrate pH=4.8
42.5% Guanidine thiocyanate
<14% Polydocanol
0.9% Dithiothreitol
Suspension of magnetic particles: 120 ul
Magnetic glass particles
93% Isopropanol
Washing buffer: 1×2.0 ml and 1×500 ul
Tris-base buffer pH=6.8
0.2% Methylparaben
Elution buffer: 65 ul
Tris-base buffer pH=7.6
0.2% Methylparaben
Adsorbent material: 2.7 g HySorb™ BASF, Ludwigshafen, Germany
Compound of interest: HBV viral DNA
Biological sample: 860 ul blood plasma A volume of 860 ul of the biological sample is added to one or more temperature-controlled chambers through a first inlet port located on the upper surface closer to the outer part of the device according to the invention. The device used comprises in total eight chambers. The sample is pretreated with lysis buffer, including a protease, e.g., Proteinase, and possibly with binding buffer (or alcohol). A portion of about 120 ul of the suspension of magnetic particles is added to the pretreated sample. Mixing and incubation of the solution in the chamber is carried out by slightly moving the rotor including the device with the eight chambers back and forward by a few degrees.

After incubation, which usually takes not more than five minutes, the components of interest are bound to the magnetic particles. The magnet is moved up, that means the magnet is switched on by introducing it in the centre of the device. Consequently, the magnetic particles are collected at the inner side at the inner wall of the chamber. By applying moderate centrifugal forces (e.g., 6×g) the sample fluid, including the non-magnetic ingredients, is expelled to the outer wall of the chamber, where the adsorbent material, for example material which is very widely used in hygiene articles, namely HySorb™ from BASF, Ludwigshafen, Germany or poly(acrylic acid), partial potassium salt, lightly crosslinked (Sigma-Aldrich ST. Louis Mo., 63103, USA) in a fibrous matrix, is positioned.

After centrifugation, when the rotating movement of the device is neutral, the magnet is pulled out of the device by moving down the magnet with the consequence that the magnetic particles, including the component of interest bound thereto, are released into the bottom of the (reaction) chamber. The suspension of magnetic particles obtained is further purified by the addition of multiple fractions of washing buffers (usually 1×2 ml and a second time a smaller volume, e.g. 500 ul, or less per chamber are sufficient) and moderate movement of the rotor device (e.g., 1- or 2-times with 6×g). Consequently, non desired ingredients of the sample are solved in the washing solution, whereas the components of interest, the nucleic acids, are bound to the magnetic particles.

When the washing procedure is completed and the last fraction of the washing buffer is eliminated from each of the chambers by moderate centrifugation movement (e.g., 6×g), the magnet has been put back in its original position in the centre of the device at that time. Consequently, the remaining washing buffer is transferred via the ascending bottom of the device into the absorbent material at the inner side of the outer wall of the device and the magnetic particles with the component of interest remain fixed to the bottom adjacent to the inner wall of the chamber.

In a next step 65 ul of elution buffer is added to each chamber comprising a purified fraction of dried magnetic particles to which the component of interest is bound. By removing the magnet from the device and moderate rotating back and forward movement the respective solution is mixed with the magnetic particles. The components of interest are consequently resuspended in the elution buffer. After elution the magnet is reinserted to its original position in the device with the consequence that the magnetic particles, without the components of interest, are collected at the respective position of the chamber. The elution buffer including the components of interest, can now be removed and collected, for example, with pipetting tips inserted through the second port covered with a flexible sheet located on the upper surface more to the inner part of the chamber.

If requested, the purified eluate can, alternatively, be directly transferred together with the HBV master mix (65 ul) into vessels, reaction tubes (15) or containers connected with a port at the bottom side of each chamber of the device, where the component of interest can, e.g., be amplified and/or further analyzed.

The inventive method and device can be applied for immunoassays in analogous manner on the information provided above in combination with the respective prior art, e.g., "The Immunoassay Handbook", David Wild, Nature Publishing Group 2001, p. 316-346.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

REFERENCE NUMERALS

1 Pipetting opening
2 Inner pipetting opening
3 Vent
4 Inner wall of the chamber
5 Lower part of the chamber
6 Inner barrier
7 Cut off trench
8 Ascending part of the lower part of the chamber
9 Gap
10 Means for trapping fluids, e.g., a hyper absorbent material
11 Housing of the chamber
12 Magnet
13 Direction of the centrifugal force
14 Direction of the magnetic force
15 Reaction tube
16 Opening of the reaction tube
17 Pipetting outlet
18 Arrow movement of the magnet
19 Rotation axis
20 Lower ascending part of the chamber
21 Magnetic particles
22 Reaction solution/reaction chamber
23 Cover
24 Partition wall
25 Outer wall of the chamber
26 Nose strip
27 Channel
28 Hinge

The invention claimed is:

1. A container for separating a component of interest bound to magnetic particles from a solution, said container comprising:

(a) one or more flat chambers wherein each flat chamber comprises an interior volume, an angular bottom ascending to an outer part of the flat chamber, a means for trapping fluids wherein the means for trapping fluid is positioned inside the outer part of the flat chamber, (b) a magnet positioned at an outer side of an inner wall of the flat chamber for capturing the magnetic particles and the component of interest bound to said magnetic particles, said magnet comprising a magnetic force in a first direction toward the outer side of the inner wall, (c) a rotation axis around which said container is configured to rotate, the rotation axis located outside the inner part of the flat chamber and adjacent to the magnet, said rotation axis comprising a centrifugal force in a second direction and toward the outer part of the flat chamber while rotating.

2. The container according to claim 1, wherein the one or more chambers each have a volume in the range from 1 ml to 50 ml.

3. The container according to claim 1, comprising multiple chambers combined in a first single cassette, connected or connectable to one or two additional single cassettes, wherein each cassette consists of from 2 to 100 chambers.

4. The container according to claim 3, wherein the single cassettes are located on a ring around the rotating axis.

5. The container according to claim 1, comprising multiple chambers arranged in single cassettes forming a linear or ring-formed array, wherein each single cassette comprises from 4 to 96 single inter-connectable containers.

6. The container according to claim 1, wherein the one or more chambers comprise at least one inlet and outlet port.

7. The container according to claim 6, wherein the inlet and outlet ports are covered with a flexible sheet or film.

8. The container according to claim 1, wherein each chamber is equipped with a vent opening.

* * * * *